(12) United States Patent
Swartz et al.

(10) Patent No.: US 6,464,144 B1
(45) Date of Patent: Oct. 15, 2002

(54) HAND HELD TERMINAL WITH AN ODOR SENSOR

(75) Inventors: Jerome Swartz, Old Field, NY (US); Thomas K. Roslak, Eastport, NY (US)

(73) Assignee: Symbol Technologies, Inc., Holtsville, NY (US)

( * ) Notice: Subject to any disclaimer, the term of this patent is extended or adjusted under 35 U.S.C. 154(b) by 0 days.

(21) Appl. No.: 09/573,582

(22) Filed: May 18, 2000

(51) Int. Cl.[7] .................................................. G06K 7/10
(52) U.S. Cl. ..................... 235/477.01; 235/375; 235/383
(58) Field of Search .......................... 235/472.01, 375, 235/383

(56) References Cited

U.S. PATENT DOCUMENTS 5,821,512 A * 10/1998 O'Hagan et al. ........... 235/383
5,918,257 A * 6/1999 Mifsud et al. ............. 73/23.34
5,979,757 A * 11/1999 Tracy et al. ................ 186/56
6,199,753 B1 * 3/2001 Tracy et al. ............... 235/375

FOREIGN PATENT DOCUMENTS

JP          3116859       * 12/2000

* cited by examiner

*Primary Examiner*—Karl D. Frech
*Assistant Examiner*—Allyson Sanders

(57) ABSTRACT

A hand held terminal has a display, a keying input, an odor sensor, a processor for receiving information from the keying input and from the odor sensor for processing same and for directing information onto the display and a housing for the keying input, odor sensor, display and processor.

7 Claims, 2 Drawing Sheets

HAND HELD TERMINAL WITH AN ODOR SENSOR

BACKGROUND OF THE INVENTION

The present invention relates to hand held terminals, and in particular to portable shopping terminals having the capability of sensing the odor of foods and the like.

Portable shopping terminals are known, for example from U.S. Pat. No. 5,923,735, the disclosure of which is hereby incorporated by reference herein. Sensor arrays for detecting odors, sometimes called electronic noses, are known and have been described in U.S. Pat. No. 6,017,440, the disclosure of which is incorporated herein by reference.

The main object of the present invention is to combine an electronic odor sensor into a terminal and specifically into a portable shopping terminal for use therewith.

SUMMARY OF THE INVENTION

In accordance with the present invention, a hand held terminal is provided having a display, a keying input which can be either manually actuated keys such as on a keyboard and/or touch screen actuated keys, an odor sensor which generates a signal corresponding to an odor that is sensed, a processor for receiving information from the keying input and from the odor sensor for processing same and for directing information onto a display. In a preferred embodiment of the present invention, a housing is provided for the terminal in which the keying input, odor sensor, display and processor are contained. The terminal also preferably includes a bar code scanner which can either be incorporated in the housing, attached to the housing, or be received as a module that can be separately plugged into an interface slot.

The odor sensor can be used to sense the odor of food in a food store for use by the terminal. For example, the terminal can use the input from the sensor to determine if food is spoiled, it can be used to identify a product, or it can be used to differentiate between products to determine price differentials.

The odor sensor can be routinely used in the home on the typical "milk smell" test and tasting the turning milk or cream in your coffee. The terminal would put the spoiled milk or cream on a shopping list so that you could order it immediately or in the next 2 days if it is sensing the slow decay of the foodstuff. The same could be used for produce in the home.

Additionally, identification of the item that you are going to scan is important as well. For example, this could be used to identify the expensive "golden delicious" apple from the less expensive "macintosh" variety.

These and other objects are the advantages of the present invention are disclosed hereinafter with reference to the attached drawings, wherein:

DETAILED DESCRIPTION OF THE INVENTION

Figure 1:
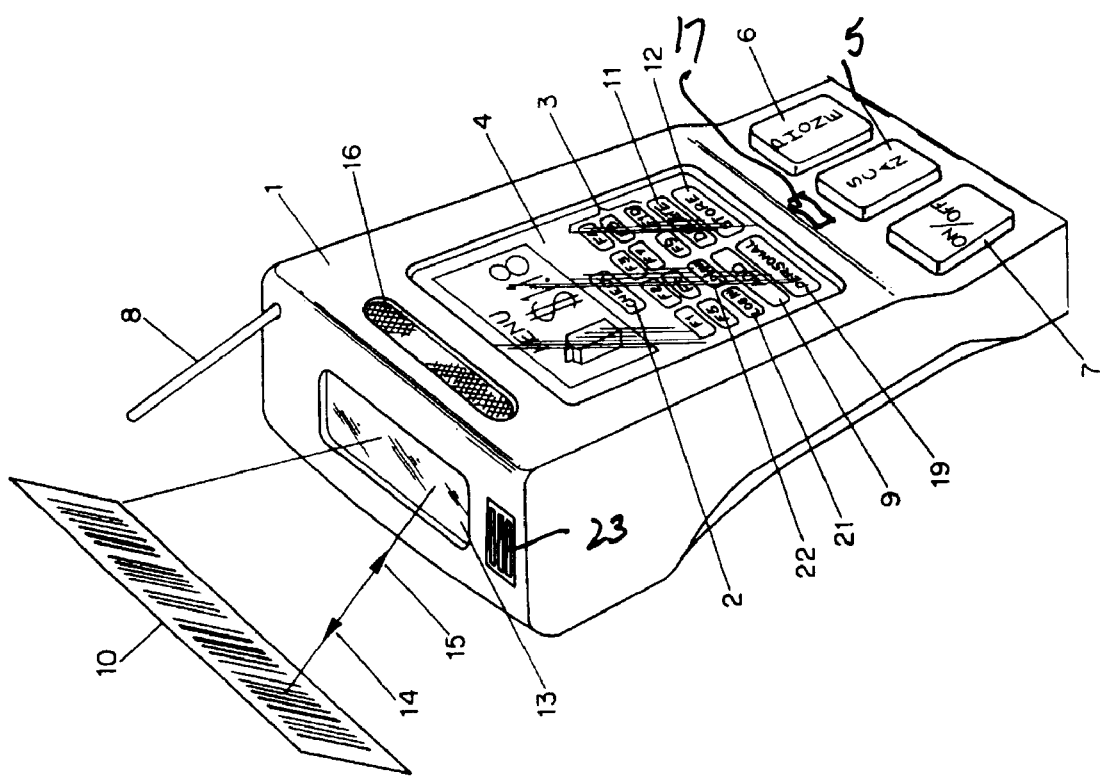
FIG. 1 shows a portable shopping terminal in accordance with the present invention.

The terminal in FIG. 1 is a portable communications terminal 1 in accordance with the invention (various minor components of the portable communications terminal have been omitted for simplicity). The terminal is one of the elements of the invented self-checkout system. Power to the device is controlled by an on/off toggle key 7. As used herein, the term "key" represents a physical push key which can be activated either manually or mechanically. Also, as used herein, the term "button" represents a touch sensitive, software programmable area of the touch screen display. The on/off key may be activated. The on/off key 7 powers up the portable communications terminal 1 when the terminal is in the off state, and powers down the device 1 when it is in the on state. There are two basic operating modes: a phone mode and a scan mode. When operating in the cellular phone mode, the portable communications terminal 1 is designed to operate as a cellular phone in accordance with the cell phones well known in the art. (Refer to U.S. Pat. Nos. 4,697,281, 4,837,800, 4,887,265). The scan mode is subdivided into a personal scan mode and a store scan mode. Store scan mode is the mode used during the self-checkout transaction.

At power-up, the device wakes up in either the phone mode or the personal scan mode. The phone key 6 places the portable communications terminal 1 into the cellular phone operating mode. The scan key 5 turns on the scan mode and allows the portable communications terminal 1 to operate as a bar code scanning terminal. Bar code scanners and scanning terminals are well known in the art. (Refer to U.S. Pat. Nos. 4,850,009, 5,015,833, 5,021,641, 5,414,251).

A touch screen 4, a speaker 16 and a microphone 17, provide visual, tactile and audio operator feedback. The microphone 17 converts acoustical voice signals into electrical signals. It is used heavily during the phone operation, but may also be utilized by a user to send voice commands to the device during scan mode operation.

Speaker 16 converts electrical signals into acoustical signals that are sent to an operator. It is used heavily during the phone mode operation, but could also be used to send the system status, via recorded messages, beeps, or music, to the user during scan mode operation.

The touch screen 4 displays information and system status, and allows the user to select different system options. Depending on the operating mode, the touch screen displays different software menus. In addition, the touch screen 4 displays different software controlled buttons or graphic control representations. Software controlled buttons change their functionality depending on the mode of the device operation. Software controlled buttons are divided into two types: user programmable software controlled touch screen buttons and mode dedicated touch screen buttons. The touch screen 4 shows the display of items when the terminal is in the scan mode of operation. Reference numeral 3 designates a group of user programmable software controlled buttons F1 through F10. By programming the functionality of the buttons F1 through F10, a user can customize the display. Personal scan button 19, store scan button 12, add button 9, delete button 11, check button 2, log-in button 21, and log-out button 22 are mode dedicated touch screen buttons. They appear on the display whenever the terminal is in the scan mode of operation, and cannot be changed by the user. Personal scan button 19 is utilized when the user wants to come out of a store scan operating mode and wants to enter the personal scan mode. Store scan button 12 is utilized when the user wants to come out of the personal scan mode and wants to enter the store scan mode. When either the personal scan mode or the store scan mode is enabled, the add button 9, the delete button 11 and the check button 2 appear on the touch screen. Selecting either one of the buttons activates scanning. Scanning may also be activated by the add, the delete, or the check voice commands into the microphone. The log-in button 21 is used to establish cellular communication channel between the terminal and a remote party during the self-checkout transaction. The log-out button 22 is used to terminate the cellular communication channel between the terminal and the remote party at the end of the self-checkout transaction.

The terminal has an opening 23 for an odor or smell sensor 36 (shown in FIG. 2) which converts odors to electrical signals processed by a processor in the terminal. The activation of the sensor 36 and the function of the sensor can be set up by menus on the display. The odor sensor can be used to sense the odor of food in a food store for use by the terminal. For example, the terminal can use the input from the sensor to determine if food is spoiled, it can be used to identify a product, or it can be used to differentiate between products to determine price differentials.

The cellular portable communications terminal 1 is designed to ease the aiming at a bar code symbol 10, when the user is attempting to scan the bar code. When scanning is activated by the add button 9, the delete button 11, the check button 2, or the voice commands, a laser beam 14 exits the terminal through a light transmitting window 13 and is reflected off of the bar code 10. The reflected light 15 is detected and processed by the circuitry inside the terminal.

The terminal uses an antenna 8 to communicate with the remote party via a cellular telephone network. When the device 1 is used as a cellular phone, the antenna 8 mostly transmits and receives voice data. When the device 1 is operated in the store scan mode, the antenna 8 transmits and receives bar code, voice and product data.

Figure 2:
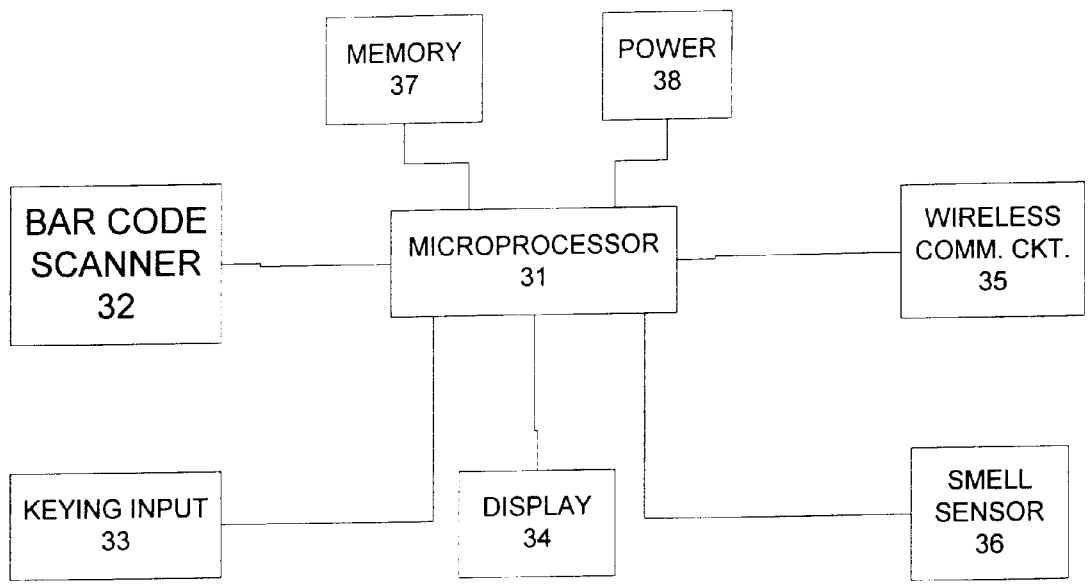
FIG. 2 is a schematic drawing of a computer system of a terminal incorporating the smell sensor according to the present invention.

FIG. 2 shows a schematic of the circuitry that interacts with the sensor. As shown, a microprocessor 31 receives inputs from a keying input 33, bar code scanner 32 and smell or odor sensor 36. The microprocessor stores data in memory 37 and displays data on the display 34. Power is supplied to the microprocessor and the remaining elements of the system via power input 38 which is a battery or a rechargeable battery. A wireless communication circuit 35 for sending an receiving data at the terminal can be a Bluetooth communication module, a WAN circuit, a LAN circuit, etc.

Figure 3:
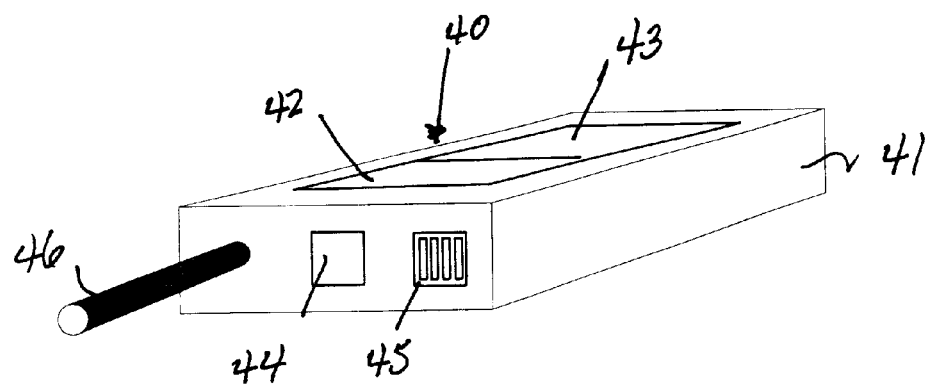
FIG. 3 shows a alternative hand held terminal incorporating a smell sensor.

FIG. 3 illustrates a general purpose terminal 40 with the sensor 36 built in. Terminal 40 has housing 41 in which is incorporated a scan engine which scans through window 44 and a wireless communications circuit which utilizes antenna 46. The terminal also has a display 42 and a keyboard 43. The sensor is behind opening 45 for sensing odors and generates a signal which is processed by the processor in the terminal.

The bar code scanner can be a laser bar code scanner, CCD imager, or other scanner and can be retroreflective or non-retroreflective.

What is claimed is:

1. A hand held portable shopping terminal comprising:

a display;

a keying input;

a memory having a shopping list stored therein;

an odor sensor configured to sense the odor of food products;

a processor for receiving information from the keying input and from the odor sensor for processing same and for directing information onto the display;

the processor further configured to maintain the shopping list; and a housing for the keying input, odor sensor, display and processor.

2. The terminal according to claim 1, wherein the odor sensor senses the odor of food in a food store for use by the terminal.

3. The terminal according to claim 1, wherein the terminal uses the input from the sensor to determine spoilage.

4. The terminal according to claim 1, wherein the terminal uses the input from the sensor to identify a product.

5. The terminal according to claim 1, wherein the terminal uses the input from the sensor to determine price differentials between food products.

6. The terminal according to claim 1, further comprising a bar code scanner.

7. The terminal according to claim 1, wherein the processor is configured to add a particular food product to the shopping list in response to the detection of an odor indicating that the particular food product is at least near spoiling.

* * * * *